(12) United States Patent  
Tsuda et al.

(10) Patent No.: US 7,406,886 B2  
(45) Date of Patent: Aug. 5, 2008

(54) INJECTOR

(75) Inventors: Takao Tsuda, 3102, Kaguyama 2-chome, Nisshin-shi, Aichi (JP); Eiji Iizuka, Nagoya (JP); Motonori Munesue, 178-11, Kitashinmachi 6-chome, Matsubara-shi, Osaka (JP)

(73) Assignees: Takao Tsuda, Aichi (JP); Chemco Scientific Co., Ltd., Osaka (JP); Motonori Munesue, Osaka (JP)

( * ) Notice: Subject to any disclaimer, the term of this patent is extended or adjusted under 35 U.S.C. 154(b) by 0 days.

(21) Appl. No.: 11/833,830

(22) Filed: Aug. 3, 2007

(65) Prior Publication Data  
US 2007/0278434 A1    Dec. 6, 2007

Related U.S. Application Data

(62) Division of application No. 10/994,124, filed on Nov. 19, 2004, now Pat. No. 7,252,016.

(30) Foreign Application Priority Data  
Nov. 27, 2003    (JP) .............................. 2003-397271

(51) Int. Cl.  
    *G01N 1/38*    (2006.01)
(52) U.S. Cl. ................. 73/863.73; 73/863.01
(58) Field of Classification Search ...... 73/863–863.01, 73/863.71–863.73, 864.81, 864.83–864.85, 73/864.87; 250/576  
See application file for complete search history.

(56) References Cited

U.S. PATENT DOCUMENTS

| | | | |
|---|---|---|---|
| 3,555,284 A * | 1/1971 | Anderson | 436/45 |
| 3,744,975 A * | 7/1973 | Mailen | 250/576 X |
| 3,856,470 A * | 12/1974 | Cullis et al. | 422/64 |
| 4,023,498 A * | 5/1977 | Harris | 250/576 X |
| 4,710,641 A | 12/1987 | Aulds et al. | |
| 5,007,740 A * | 4/1991 | Jeannotte et al. | 250/576 X |
| 5,059,025 A | 10/1991 | Ando | |
| 5,651,614 A | 7/1997 | Juneau | |

(Continued)

FOREIGN PATENT DOCUMENTS

JP    61-275639 A    12/1986

(Continued)

*Primary Examiner*—Thomas P Noland  
(74) *Attorney, Agent, or Firm*—Panitch Schwarze Belisario & Nadel LLP

(57) ABSTRACT

An injector has a sample chamber for retaining a small amount of sample, wherein a position of the sample chamber is controlled by transmitting light through the sample chamber and detecting the transmitted light so as to recognize the position of the sample chamber. It is possible to reduce detection error compared to the conventional injectors that indirectly control the position of the sample chamber by transmitting light through the light passage which is adjacent to the sample chamber. A method for injecting a sample comprising the steps of: providing an injector which has a sample chamber for retaining a sample with an open month; transmitting light through the sample chamber; detecting the transmitted light so as to recognize a position of the sample chamber; and controlling the position of the sample chamber by using the detection result to connect the open month of the sample chamber to an open month of a sample receiving member in order to inject the sample into the sample receiving member.

8 Claims, 7 Drawing Sheets

U.S. PATENT DOCUMENTS

| | | |
|---|---|---|
| 5,930,033 A | 7/1999 | Inoue et al. |
| 6,992,759 B2 | 1/2006 | Nakayama et al. |
| 2002/0112530 A1 | 8/2002 | Kitagawa |
| 2003/0148536 A1 | 8/2003 | Liang et al. |
| 2005/0126312 A1* | 6/2005 | Bedingham et al. ...... 73/863.01 |
| 2005/0130177 A1* | 6/2005 | Bedingham et al. ... 73/863.01 X |

FOREIGN PATENT DOCUMENTS

JP  2000-186985 A  7/2000

* cited by examiner

INJECTOR

CROSS-REFERENCE TO RELATED APPLICATIONS

This application is a divisional of U.S. patent application Ser. No. 10/994,124, filed Nov. 19, 2004, now U.S. Pat. No. 7,252,016, issued Aug. 7, 2007, the disclosure of which is incorporated herein by reference.

BACKGROUND OF THE INVENTION

This invention relates to an injector, for example, of a rotary type, especially used in chromatography.

Japanese Patent Application Publication Laid-Open No. 2000-186985, the disclosure of which is herein incorporated by reference, discloses a micro-injector which is generally used in liquid chromatography.

As shown in FIG. 7, the above type of injector, which is a rotor 21, includes a sample chamber 22 (a flow channel) for a sample eluent to pass through and a light passage 23, both of which are provided in the rotor 21. The position of the sample chamber 22 is recognized by transmitting light through the light passage 23 and detecting the transmitted light with a light detector and, thus, the position of the sample chamber 22 is indirectly controlled.

However, since the internal diameter of the sample chamber 22 is so small, it is required to control the position of the sample chamber 22 with accuracy down to the micrometer in order to connect the sample chamber 22 to an open mouth of a capillary column at the downstream end of the sample chamber 22.

Therefore, an object of the present invention is to provide an injector that has an accurately position-controllable sample chamber.

BRIEF SUMMARY OF THE INVENTION

The present invention provides an injector having the following technical features to achieve the above object.

(1) An injector according to the present invention has a sample chamber for retaining a small amount of sample, wherein a position of the sample chamber is directly controlled by transmitting light through the sample chamber and detecting the transmitted light so as to recognize the position of the sample chamber.

In this injector, since the position of the sample chamber is directly controlled by transmitting light through the sample chamber and detecting the transmitted light, it is possible to reduce detection error compared to the conventional injectors that indirectly control the position of the sample chamber by transmitting light through the light passage which is adjacent to the sample chamber.

(2) The above injector may be a rotor (a rotary type injector), wherein the sample chamber is provided in the rotor and the rotation of the rotor is controlled by transmitting light through the sample chamber and detecting the transmitted light so as to recognize the position of the sample chamber.

This feature allows a smooth operation of the rotary type injector because the sample chamber is provided in the rotor.

(3) The above injector may further have an optically transparent capillary tube and the sample chamber may be provided in the capillary tube.

This feature allows a greater amount of light transmission through the sample chamber because, when light comes into the sample chamber, the light is transmitted through not only a hollow portion of the capillary tube (the sample chamber) through which the sample flows, but also the capillary tube itself. Since the amount of light transmitted through the sample chamber is increased, it becomes easier to detect the light transmitted through the sample chamber.

(4) As the optically transparent capillary tube, a fused silica capillary tube may be used.

This feature allows an even greater amount of light transmission, because the fused silica capillary tube, which is made of glass, has better optical transparency than a PEEK tube or the like; so that it becomes possible to carry out better direct control of the position of the sample chamber.

(5) In the above injector, the sample chamber may be connected with a light-conducting capillary tube at the upstream end of the sample chamber, wherein the light-conducting capillary tube is a polytetrafluoroethylene tube filled with a mixed solution of water and ethanol.

This feature allows efficient irradiation of light to the sample chamber because an optical fiber, which has superior light conductivity, is formed by having the wall surface of the polytetrafluoroethylene tube as a cladding and the mixed solution as a core.

(6) The above fused silica capillary tube may have an external wall coated with an optically transparent resin.

This feature allows a greater amount of light transmission to a light detector afterwards, because the resin coated on the external wall of the capillary tube improves the light-transmitting ability of the capillary tube because of its optical transparency.

This fused silica capillary tube with the external wall coated with the optically transparent resin may be used not only as the capillary tube of the sample chamber but also as the capillary column which is connected with the sample chamber at the downstream end.

(7) A stationary phase which is capable of holding a sample may be provided to an internal wall of the above capillary tube.

This feature allows the sample chamber to retain a large amount of sample, because the sample is retained not only in the sample solvent which is filled in the sample chamber but also in the stationary phase which is provided to the internal wall of the capillary tube. As the stationary phase, chemically-modified octadecylsilane may be provided to the internal wall of the capillary tube.

(8) The light which is transmitted through the sample chamber may be a laser light. The laser light allows more accurate control of the position of the sample chamber because it has stronger light intensity.

(9) The above stationary phase may be made so as to release the sample which is held therein as the temperature of the sample chamber is increased by the light which is used to recognize the position of the sample chamber.

Since the capillary tube is heated up when it receives light, the sample which is held in the stationary phase (e.g. octadecylsilane) can be released therefrom. Therefore, the light transmitted through the capillary tube can be used to recognize the position of the sample chamber and, at the same time, can also be used to release the sample from the stationary phase. This makes it possible for the sample chamber to retain a large amount of sample in the space thereof.

The present invention composed as above has the following effects.

An injector according to the present invention can control the position of the sample chamber by transmitting light directly through the sample chamber and detecting the transmitted light so as to recognize the position of the sample chamber, so that it is possible to reduce detection error and allow more accurate control of the position of the sample compared to the conventional injectors.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
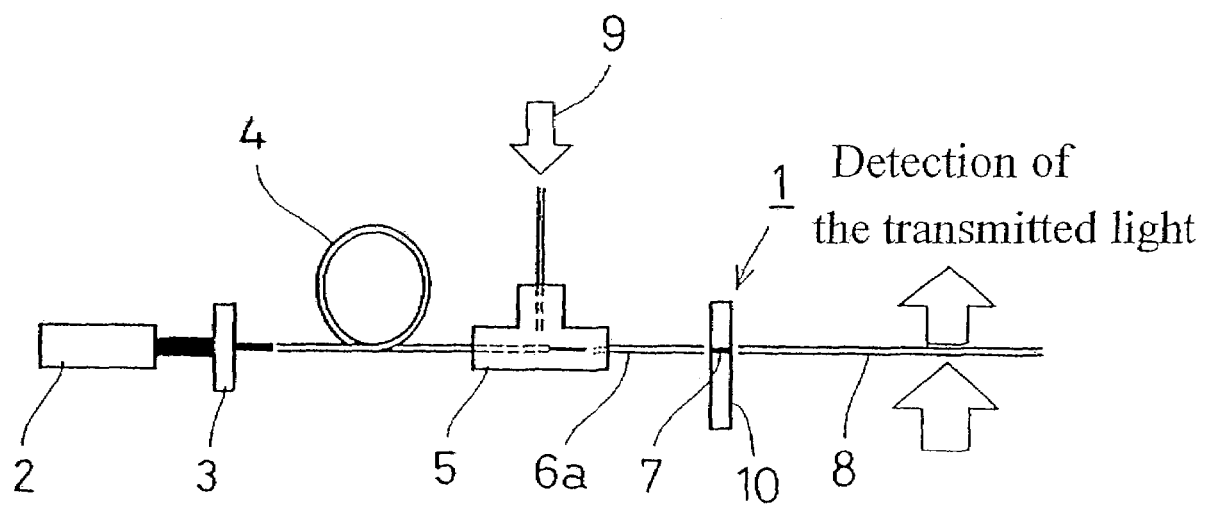
FIG. 1 is a diagrammatic illustration demonstrating a system including an injector which is a rotor according to the present invention.

Referring to Figures, the following description will discuss embodiments of the present invention.

As shown in FIGS. 1-6, in a rotary type injector 1 of this embodiment according to the present invention, a laser light (a light ray) which is generated by a laser generator 2 is transmitted into a sample chamber 7 (a sample flow channel) through a lens 3, an optical fiber 4, a three-way connector 5 and a light conducting-capillary tube 6a, and then the laser light reaches to a capillary column 8. The sample chamber 7 is provided in an optically transparent capillary tube 6b. A small amount of sample is supplied into the sample chamber 7 by a constant pressure pump 9 through the three-way connector 5.

Figure 2:
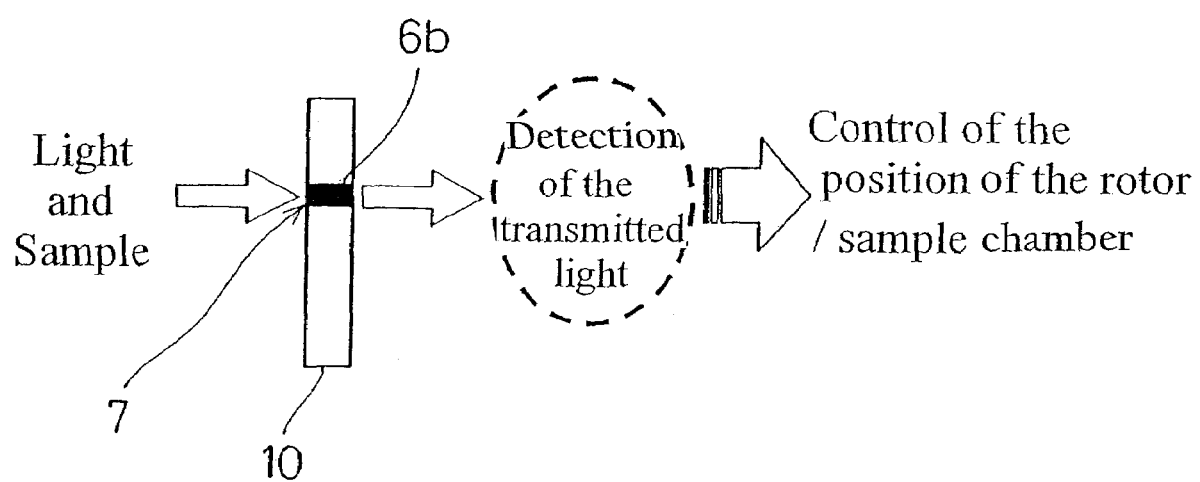
FIG. 2 is a diagrammatic illustration demonstrating the injector shown in FIG. 1.
Figure 3:
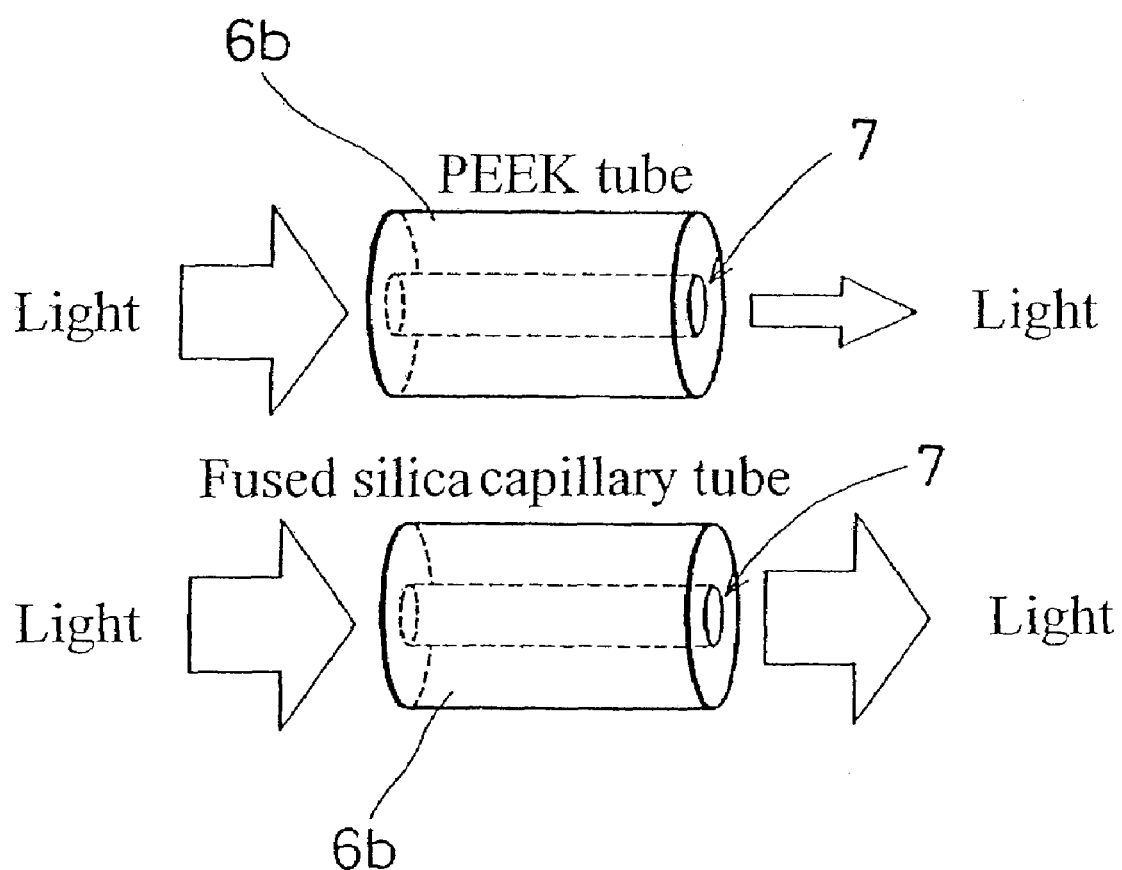
FIG. 3 is a diagrammatic illustration demonstrating a difference between the amount of light respectively transmitted through sample chambers of capillary tubes made of different materials.

As shown in FIGS. 1 and 2, the rotary type injector 1 (the rotor 10) includes the capillary tube 6b, and the sample chamber 7 in which a small amount of sample is retained. As shown in FIGS. 2 and 3, the sample chamber 7 is provided in the capillary tube 6b which is a hollow capillary tube and has optical transparency.

Instead of using the optically transparent capillary tube as the capillary tube 6b provided in the injector 1, it is more preferable to use a fused silica capillary tube, an external wall of which is coated with an ultraviolet radiation transmission resin (an optically transparent resin).

An internal wall of the fused silica capillary tube may be provided with a silica gel fixed thereto, and the silica gel may be chemically modified by octadecylsilane.

As shown in FIGS. 2 and 3, the position of the rotor 10 having the sample chamber 7 is controlled by recognizing the position of the sample chamber 7 by transmitting laser light through the sample chamber 7 and detecting the transmitted laser light. The sample chamber 7 functions as a passage for both the laser light and the eluent (the small amount of sample) to pass through.

The fused silica capillary tube, the external wall of which is coated with an ultraviolet radiation transmission resin (an optically transparent resin), is also used as the capillary column 8 which is connected with the downstream end of the sample chamber 7. However, CElect™-UVT™, which is made of an optically transparent resin, may be used as the capillary column 8 instead.

A polytetrafluoroethylene tube (having a light refractive index of 1.29), which is filled with a mixed solution of water (having a light refractive index of 1.333) and ethanol (having a light refractive index of 1.359), is used as the light-conducting capillary tube 6a which is connected with the upstream end of the sample chamber 7. If the water and the ethanol are mixed at the rate of approximately 50:50 to make the mixed solution, a greater amount of light is transmitted through the light-conducting capillary tube 6a. For example, Teflon® may be used as the polytetrafluoroethylene.

Next, usage of the rotary type injector of this embodiment is described below.

In this rotary type injector 1, the optically transparent capillary tube 6b provides the sample chamber 7 for retaining a small amount of sample. The position of the sample chamber 7 (the rotation of the rotor 10) is controlled by recognizing the position of the sample chamber 7 by transmitting laser light through the sample chamber 7 and detecting the transmitted laser light. When light comes into the capillary tube 6b, the light is transmitted through the wall portion of the capillary tube 6b as well as the hollow portion of the capillary tube 6b through which the sample flows, because the capillary tube 6b is made of a material which has optical transparency.

Figure 7:
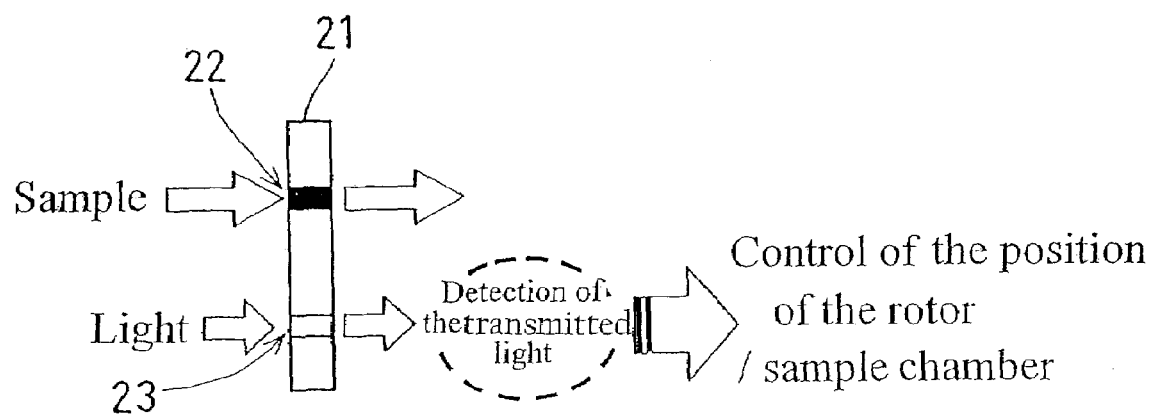
FIG. 7 is a diagrammatic illustration demonstrating an injector of the prior art which is a rotor.

Therefore, as shown in FIGS. 2 and 3, because the capillary tube 6b has optical transparency, a greater amount of light can be transmitted through the sample chamber 7, and this makes it easier to detect the light transmitted through the sample chamber 7. Consequently, the position of the sample chamber 7 can be controlled directly and even more accurately by detecting the light transmitted through the sample chamber 7, compared to the conventional injector (FIG. 7) which indirectly controls the sample chamber 22 by transmitting light through the light passage 23, which is adjacent to the sample chamber 7, and detecting the transmitted light as shown in FIG. 7.

As shown in FIG. 3, if a fused silica capillary tube is used as the capillary tube 6b, it shows greater optical transparency than a polyetheretherketone (PEEK) tube, because it is made of glass. Therefore, a greater amount of light can be transmitted through the sample chamber 7, and the direct control of the position of the injector can be carried out even more accurately.

Furthermore, if the external wall of the fused silica capillary is coated with an ultraviolet radiation transmission resin (an optically transparent resin), the fused silica capillary has a better light-transmitting ability and allows a greater amount of light transmission to a light-detector.

Additionally, if the polytetrafluoroethylene tube (having a light refractive index of 1.29) which is filled with the mixed solution of water (having a light refractive index of 1.333) and ethanol (having a light refractive index of 1.359) is used as the light-conducting capillary tube 6a which is connected with the injector at the upstream end of the sample chamber 7, it is possible to form an optical fiber by having the wall surface of the polytetrafluoroethylene tube as a cladding and the mixed solution as a core, and the light-conducting capillary tube 6a has an excellent light transmitting ability so as to transmit light to the sample chamber 7 efficiently.

EXAMPLE 1

The detailed structure of an embodiment of the present invention is described below.

To evaluate the difference in an amount of the light transmitted through the sample chamber 7 when different materials are used as the capillary tube 6b provided in the rotor 10, as shown in FIGS. 1-3, a PEEK tube and a fused silica capillary tube were selected for the capillary tube 6b in this example.

A laser light (having a wavelength of 650 to 700 nm), which was generated by the laser generator 2, was condensed by the lens 3 and then transmitted to the three-way connector 5 through the optical fiber 4. The laser light was further transmitted through the light-conducting capillary tube 6a and entered into the sample chamber 7 having an internal diameter of 50 to 100 μm provided in the capillary tube 6b and, finally, the transmitted laser light was detected by the light-detector.

The stationary phase, such as octadecylsilane, which is provided to the sample chamber 7, is heated up by the transmitted laser light, so that the sample held in the stationary phase can be released therefrom. Specifically, methyl benzoate, used as the sample in this example, which had been held in a stationary phase, was released from the stationary phase as a result of a temperature rise of the sample chamber 7.

As described above, if the fused silica capillary tube is used as the capillary tube 6b for the sample chamber 7, the amount of the transmitted laser light is increased; therefore, the fused silica capillary tube is suitable for transmitting light. This may be because the fused silica capillary tube is made of glass and the light is transmitted through both the hollow portion of the fused silica capillary tube (the sample chamber 7) and the glass wall or glass portion of the tube itself. Therefore, it is effective for the rotary type injector 1, in terms of the direct control of the position, that a glass tube having superior optical transparency, such as the fused silica capillary tube, is selected as the capillary tube 6b for the sample chamber 7.

EXAMPLE 2

An angle of the rotor 10 showing a predetermined amount of a transmitted light through the sample chamber 7 was measured, and this result was used for controlling the angle of rotation of the rotor 10 accurately.

The sample chamber 7 was provided at a distance of 5.8 mm from the rotational axis of the rotor 10. The diameter of the sample chamber 7 was 100 μm, and the diameter of the column 8 to be connected with the sample chamber 7 was also 100 μm.

Figure 4:
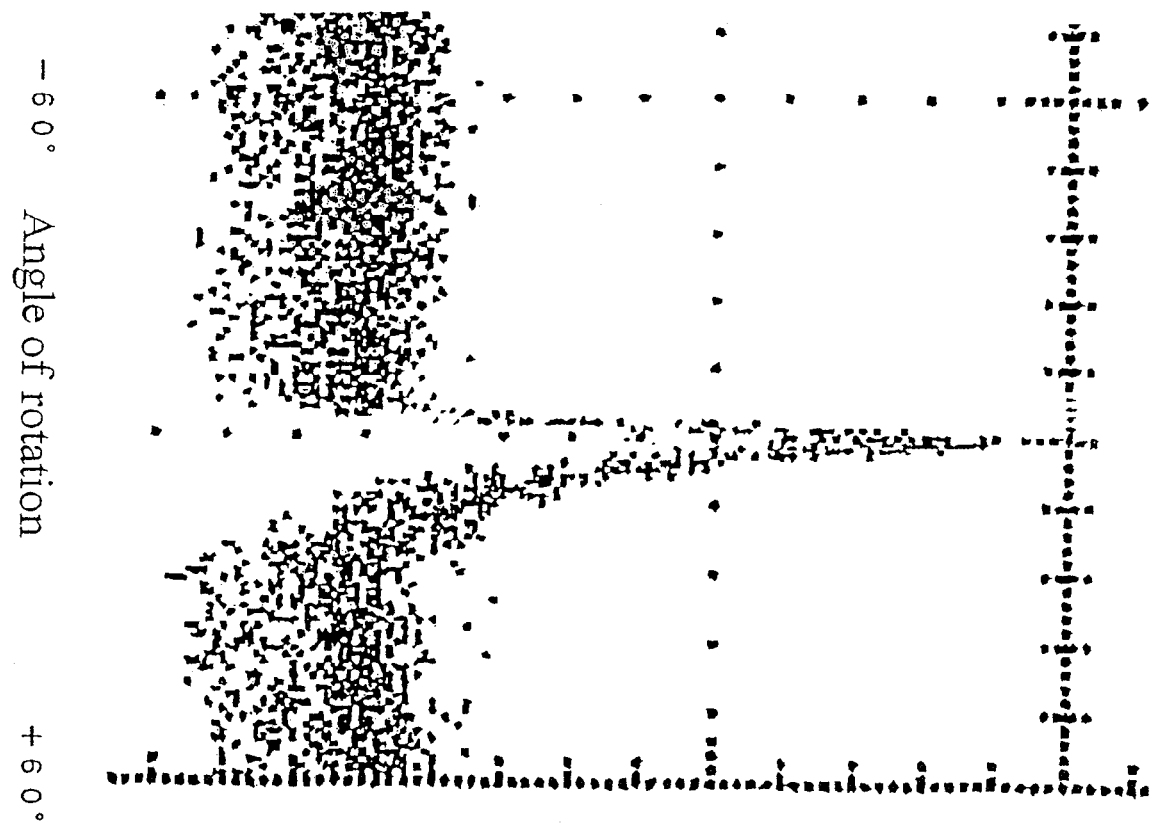
FIG. 4 is a graph demonstrating a relationship between an angle of rotation of a rotor and relative intensity of light transmitted through a sample chamber according to the present invention.
Figure 5:
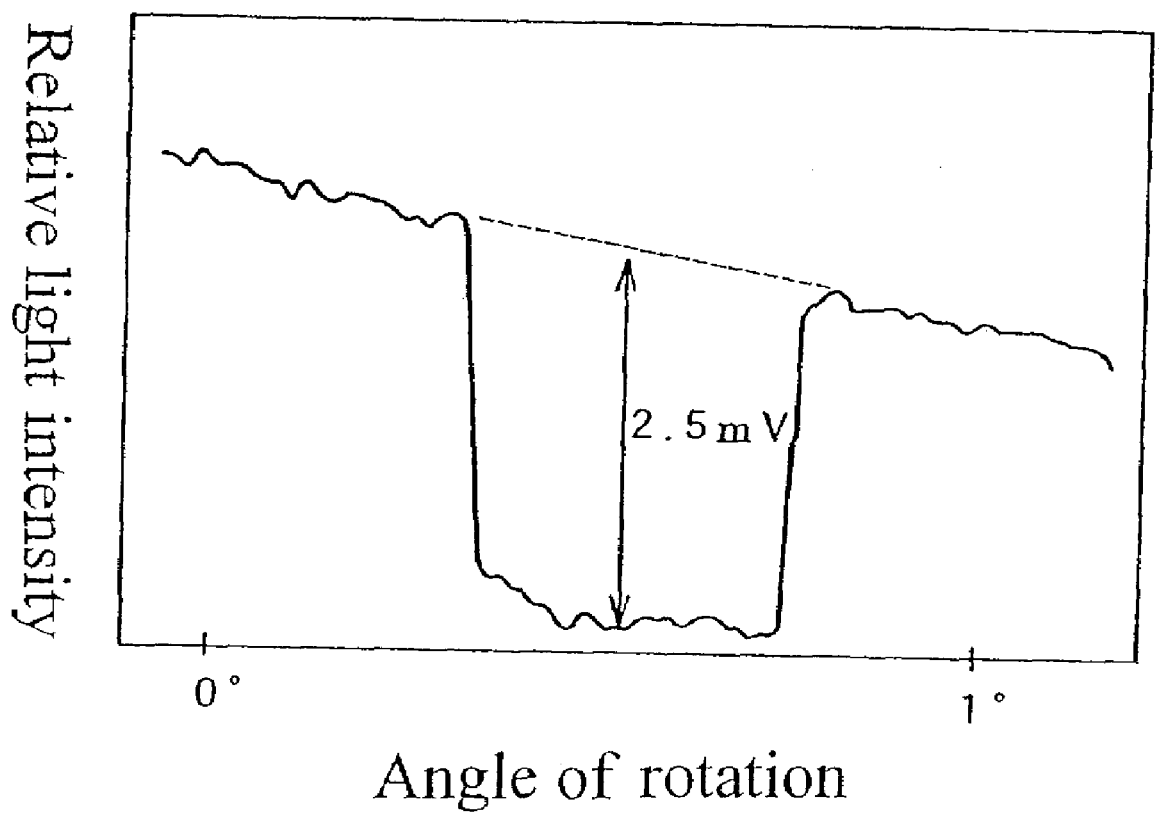
FIG. 5 is a graph demonstrating a relationship between an angle of rotation of a rotor and relative intensity of light transmitted through a sample chamber of a fused silica capillary tube according to the present invention.
Figure 6:
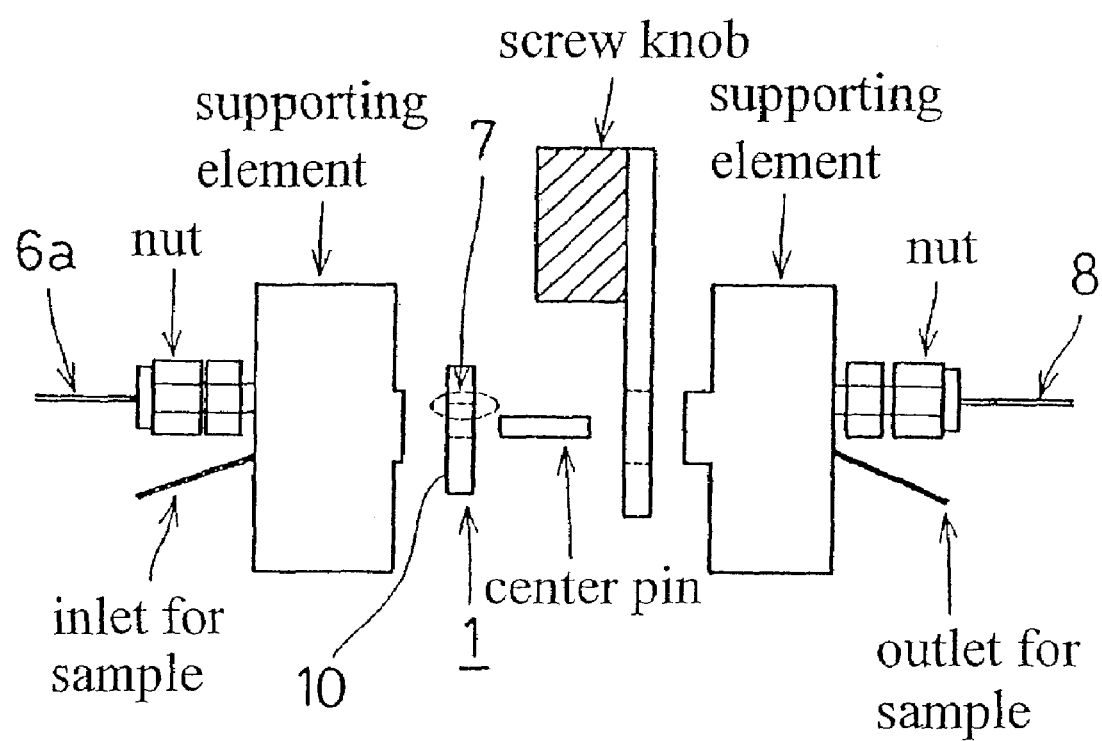
FIG. 6 is a diagrammatic illustration demonstrating a system including an injector for injecting a small amount of sample according to the present invention.

FIG. 4 is a graph showing a relationship between an angle of rotation (from −60° to +60°) and an amount of the transmitted light (relative light intensity). FIG. 5 is a graph showing a relationship between an angle of rotation (from 0° to 1°) and a signal corresponding to an amount of the transmitted light (relative light intensity). The signal was converted to "0" when the transmitted light intensity was below the predetermined amount, while the signal was converted to "1" when the transmitted light intensity was above the predetermined amount.

As a result, the rotation error has to be kept at 0.05° or less to maintain the displacement of the sample chamber 7 from the corresponding column within 10%. However, if the diameter of the sample chamber and the diameter of the column to be connected to the sample chamber were both 30 μm, the rotation error has to be kept within 0.01° to maintain the above displacement within 10%.

Consequently, the above described structure allows a precise adjustment of the position of the sample chamber 7.

This injector is capable of controlling the position of the sample chamber 7 accurately with less error, because the position of the sample chamber is recognized by transmitting light directly through the sample chamber and detecting the transmitted light, so that the injector can be applied for various usage, such as a microinjector for liquid chromatography.

It will be appreciated by those skilled in the art that changes could be made to the embodiments described without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for injecting a small amount of sample into a sample receiving member, the apparatus comprising:
    a rotor having a sample chamber with an inlet for receiving a sample and an outlet for transmitting the sample;
    a light generating device disposed upstream of the rotor;
    a light detection device disposed downstream of the rotor; and
    a sample receiving member to receive the sample from the sample chamber;
    wherein the rotor is rotatable between the light generating device and the light detection device, such that when the sample chamber is rotated to a position where light generated by the light generating device passes through the sample chamber and is detected by the light detection device, the apparatus recognizes that the sample chamber is in a correct position to release and transmit the sample to be injected into the sample receiving member.

2. The apparatus according to claim 1, wherein the light is a laser light.

3. The apparatus according to claim 1, further comprising a light-conducting capillary tube disposed upstream of the rotor, wherein the light-conducting capillary tube is a polytetrafluoroethylene tube containing a mixture of water and ethanol.

4. The apparatus according to claim 1, further comprising an optically transparent capillary tube, wherein the sample chamber is disposed within the optically transparent capillary tube.

5. The apparatus according to claim 4, wherein the optically transparent capillary tube is a fused silica capillary tube.

6. The apparatus according to claim 5, wherein an external wall of the fused silica capillary is coated with an optically transparent resin.

7. The apparatus according to claim 5, wherein an internal wall of the fused silica capillary tube is coated with a stationary phase capable of retaining at least a portion of the sample to be injected.

8. The apparatus according to claim 7, wherein the stationary phase is capable of releasing the sample retained therein, such that when there is an increase in temperature of the sample chamber due to passage of the generated light therethrough, the stationary phase releases the retained sample for transmission to the sample receiving member.

* * * * *